United States Patent
Bartholomaus et al.

(10) Patent No.: US 9,132,101 B2
(45) Date of Patent: Sep. 15, 2015

(54) ADMINISTRATION FORM BASED ON CROSS-LINKED HYDROPHILIC POLYMERS

(75) Inventors: Johannes Bartholomaus, Aachen (DE); Maria Cristina Vázquez Lantes, Munich (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 2021 days.

(21) Appl. No.: 10/596,194

(22) PCT Filed: Dec. 13, 2004

(86) PCT No.: PCT/EP2004/014146
§ 371 (c)(1), (2), (4) Date: Jun. 2, 2006

(87) PCT Pub. No.: WO2005/055991
PCT Pub. Date: Jun. 23, 2005

(65) Prior Publication Data
US 2007/0071796 A1    Mar. 29, 2007

(30) Foreign Application Priority Data
Dec. 12, 2003  (DE) .................................. 103 58 747

(51) Int. Cl.
*A61K 9/70* (2006.01)
*A61K 9/00* (2006.01)

(52) U.S. Cl.
CPC .............. *A61K 9/7053* (2013.01); *A61K 9/006* (2013.01); *A61K 9/7007* (2013.01); *A61K 9/7084* (2013.01)

(58) Field of Classification Search
CPC ................................................... A61K 9/7053
USPC ....................................................... 424/435
See application file for complete search history.

(56) References Cited

U.S. PATENT DOCUMENTS

| 4,199,569 A | | 4/1980 | Chabala et al. | |
| 4,389,397 A | | 6/1983 | Lo et al. | |
| 5,582,836 A | * | 12/1996 | Carli et al. | 424/449 |
| 6,153,222 A | * | 11/2000 | Becher | 424/486 |
| 6,177,096 B1 | * | 1/2001 | Zerbe et al. | 424/435 |
| 6,780,504 B2 | * | 8/2004 | Rupprecht et al. | 428/354 |
| 6,946,146 B2 | * | 9/2005 | Mulye | 424/479 |
| 2003/0099692 A1 | * | 5/2003 | Lydzinski et al. | 424/443 |

FOREIGN PATENT DOCUMENTS

| DE | 31 28 815 A1 | 6/1982 |
| DE | 199 32 603 A1 | 1/2001 |
| DE | 101 46 251 A1 | 4/2003 |
| EP | 0 303 445 A1 | 2/1989 |
| EP | 1 317 933 A1 | 6/2003 |

OTHER PUBLICATIONS

Campbell et al., Ivermectin: A Potent New Antiparasitic Agent, Science, vol. 221, Aug. 26, 1983, pp. 823-828.
Patent Abstracts of Japan, publication No. 06-346029, published on Dec. 20, 1994, application No. 05-140570 filed on Jun. 11, 1993.
Patent Abstracts of Japan, publication No. 2003-292554 published on Oct. 15, 2003, application No. 2002-104713 filed on Apr. 8, 2002.

* cited by examiner

*Primary Examiner* — Gina Justice
(74) *Attorney, Agent, or Firm* — Frommmer Lawerence & Haug

(57) ABSTRACT

The invention relates to a film-shaped administration form for surface administration of at least one active ingredient and/or foodstuff to a living thing. Said administration form comprises at least one layer containing an active ingredient and/or foodstuff, said layer being based on cross-linked hydrophilic polymers and containing 20 wt.-% glycerine as a softener, in relation to the total amount of cross-linked hydrophilic polymers.

16 Claims, 3 Drawing Sheets

ADMINISTRATION FORM BASED ON CROSS-LINKED HYDROPHILIC POLYMERS

Figure 1:
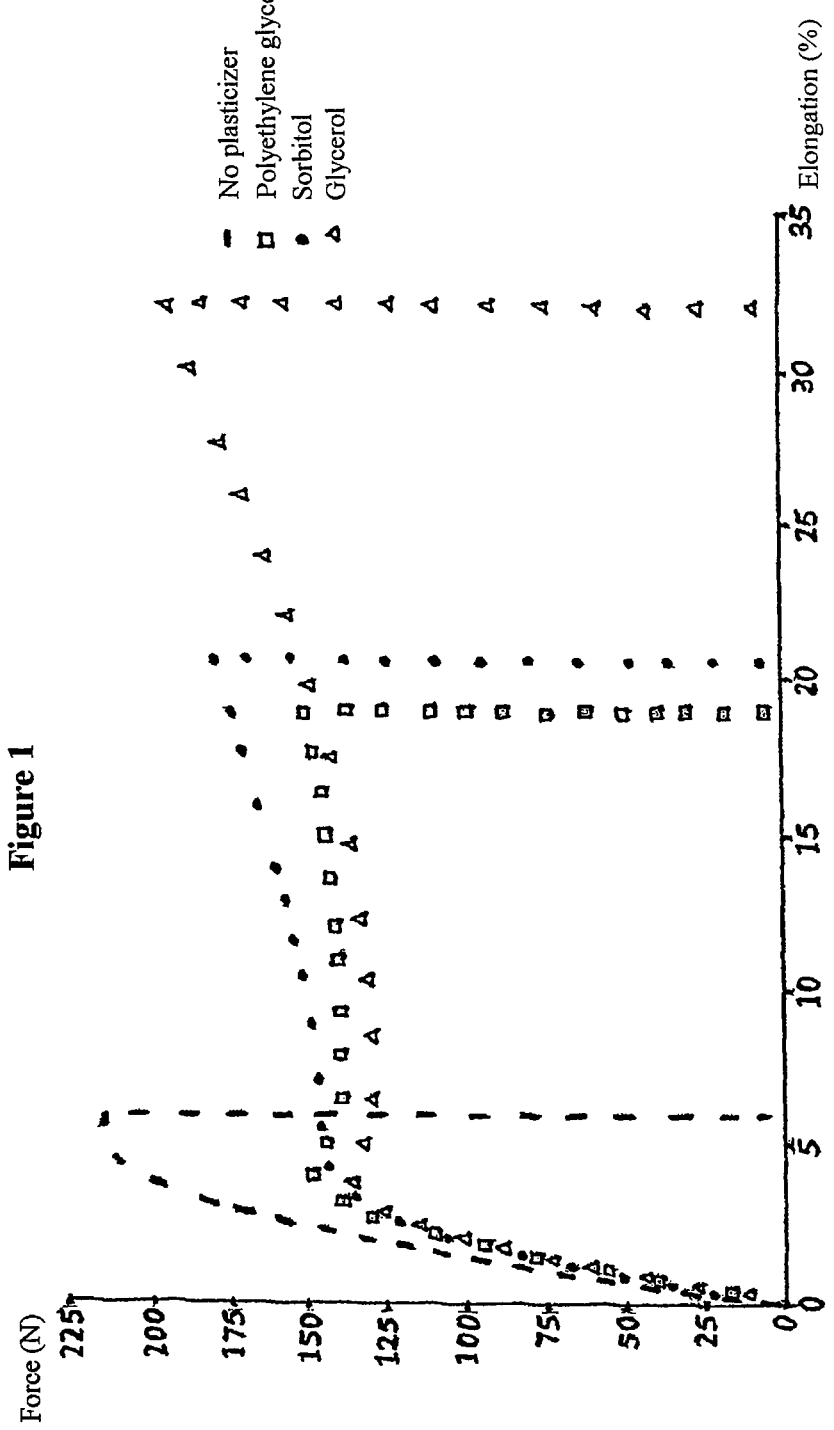
Figure 2:
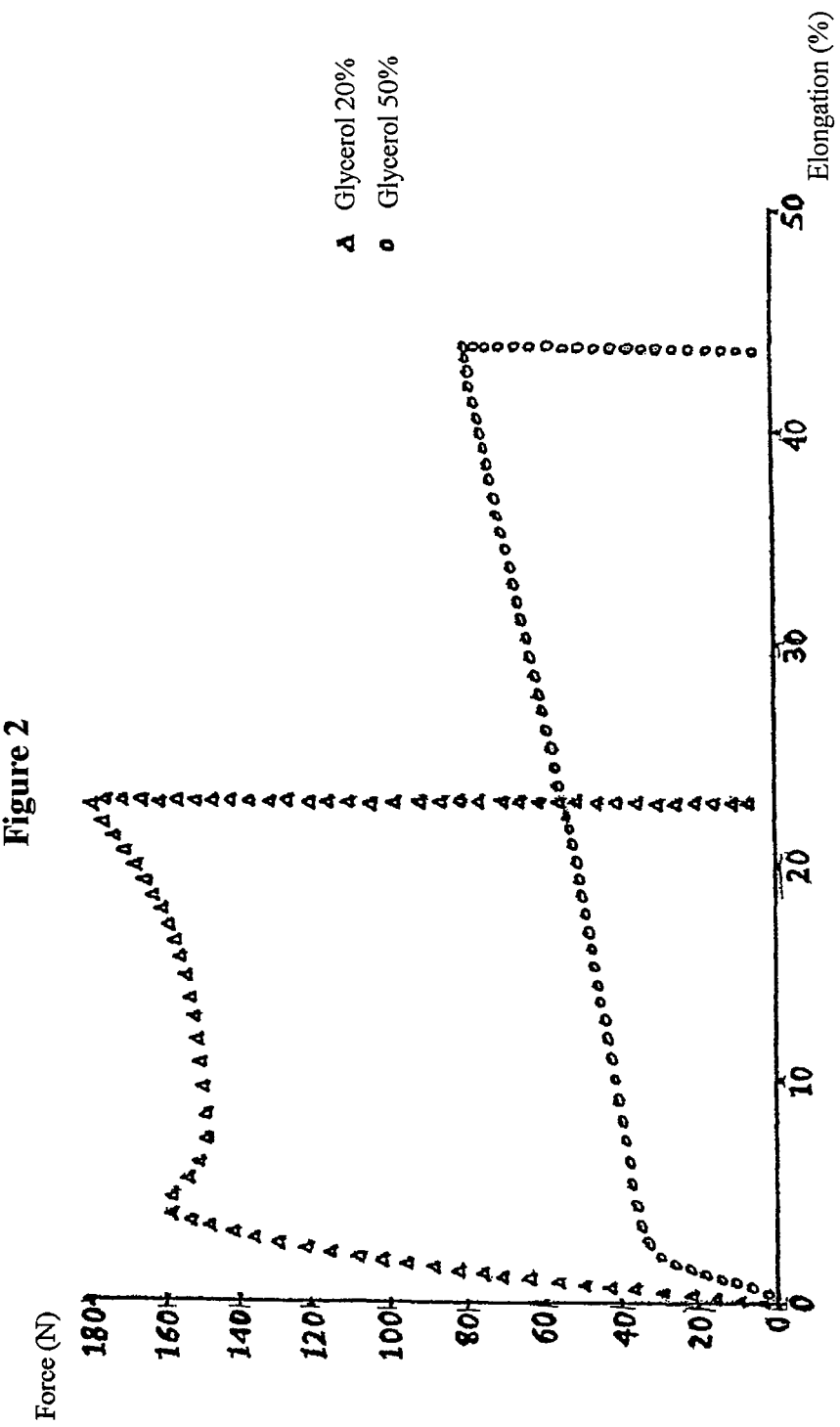
Figure 3:
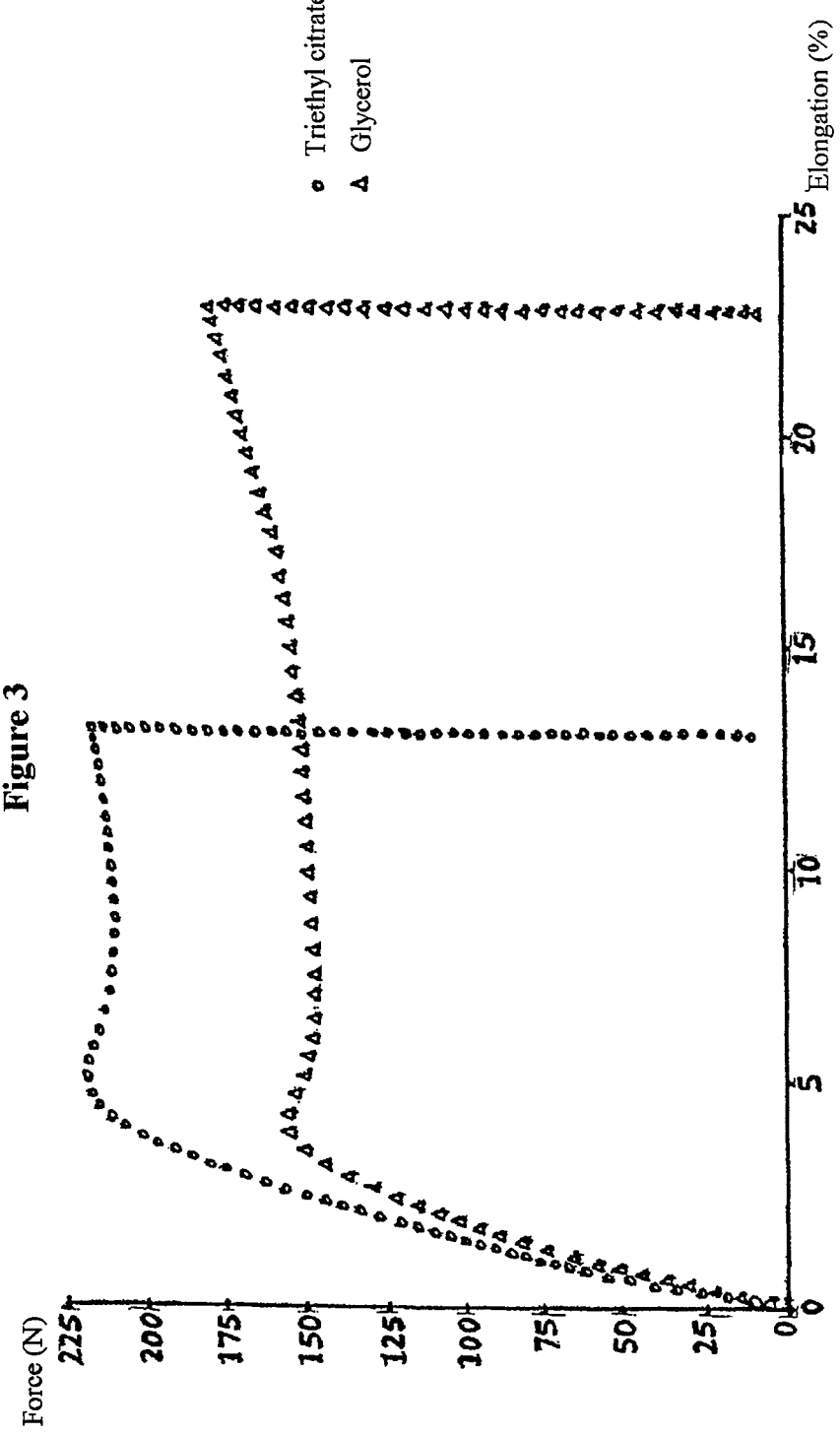

The present invention relates to a dosage form in film form for surface administration of at least one active ingredient and/or nutrient to a living creature comprising at least one active ingredient-containing and/or nutrient-containing layer based on crosslinked hydrophilic polymers which comprises=20% by weight, based on the total amount of crosslinked hydrophilic polymers, of glycerol as plasticizer.

Dosage forms in film form and made of crosslinked hydrophilic polymers can be employed for the surface administration to a living creature of active ingredients and/or nutrients which are in the form of a molecular or particulate dispersion in the active ingredient-containing and/or nutrient-containing layer.

Corresponding dosage forms in film form and made of crosslinked hydrophilic polymers for surface administration to a living creature of active ingredients and/or nutrients are described in German published specification DE 199 32 603 A1. Although such dosage forms in film form and made of crosslinked hydrophilic polymers have good plasticity in the moist state, they are more or less rigid, depending on the layer thickness, in the dry state. This low plasticity in the dry state may considerably impede surface administration of at least one active ingredient and/or nutrient to a living creature, such as, for example, on a human nasal or buccal mucosa.

The object therefore was to provide a dosage form in film form for surface administration of at least one active ingredient and/or nutrient to a living creature made of a layer based on crosslinked hydrophilic polymers, which ensures improved handling, in particular improved application of the dosage form to the surface of a living creature.

This object has been achieved by providing the dosage form of the invention in film form for the surface administration of at least one active ingredient and/or nutrient to a living creature comprising at least one active ingredient-containing and/or nutrient-containing layer based on crosslinked hydrophilic polymers, which comprises=20% by weight, based on the total amount of crosslinked hydrophilic polymers, of glycerol as plasticizer.

Living creatures within the meaning of the claimed invention are humans, animals and plants, preferably humans and animals, particularly preferably humans.

The claimed invention relates very particularly preferably to the transdermal or transmucosal administration, especially transmucosal administration, of at least one active ingredient to humans.

Normally, for better handling of relatively brittle polymer films, i.e. in particular to increase the elasticity, softness and flexibility, plasticizers are employed in an amount of up to 20% by weight based on the amount of polymer.

When the percentage amounts of plasticizer are relatively high, phase separations may occur, e.g. due to crystallization, so that the films are no longer transparent and their physical properties such as the tear strength are adversely affected. For example, addition of 30% by weight of triethyl citrate, based on the total amount of a crosslinked hydrophilic polymer, leads to white films. The plasticizer may in fact separate out of the film.

It is surprisingly possible according to the invention to incorporate large amounts of glycerol into the active ingredient-containing and/or nutrient-containing layer based on crosslinked hydrophilic polymers, and thus to achieve the necessary improvement in plasticity without occurrence of the prior art disadvantages.

The skilled worker will appreciate that the necessary amount of glycerol also depends on the thickness of the particular layer of crosslinked hydrophilic polymers. In general, the required amount is =20% by weight, preferably in the range from 20% by weight to 60% by weight, based on the total amount of crosslinked hydrophilic polymers, particularly preferably from 30% by weight to 60% by weight, the intention being that more glycerol is used for thicker layers than for thinner layers in order to achieve the same effect.

The hydrophilic polymers employed to produce the dosage form of the invention are preferably water-soluble cellulose ether, particularly preferably hydroxypropylmethylcellulose, hydroxyethylcellulose and/or methylcellulose, very particularly preferably hydroxypropylmethylcellulose.

The hydrophilic polymers are crosslinked, with in situ crosslinking preferably taking place.

This in situ crosslinking of the film-forming layer based on hydrophilic polymers preferably takes place during formation of the layer with the aid of known crosslinkers, preferably phenolic crosslinkers and/or polyacrylic acid derivatives, particularly preferably tannin and/or a crosslinked, optionally partially neutralized polyacrylic acid (Polycarbophil®). It has emerged that a ratio of hydrophilic polymer to crosslinker of from 2:1 to 5:1 by weight is suitable, and a ratio of 4:1 by weight has emerged as particularly suitable. It is possible by the crosslinking of the film-forming hydrophilic polymers to ensure sufficiently secure handling of the dosage form in film form, e.g. on removal from the package and application of the dosage form to the surface of a living creature, without damaging the dosage form by tearing. The crosslinking makes it possible according to the invention to provide dosage forms in film form with a minimum tear strength of 40 N, preferably of at least 50 N, particularly preferably of at least 60 N.

The dosage form of the invention in film form is employed for the surface administration of at least one active ingredient and/or nutrient to a living creature.

There is in principle no restriction on the active ingredients and/or nutrients contained in the active ingredient-containing and/or nutrient-containing layer. The active ingredients or nutrients are, however, preferably fragrances, flavorings, diagnostic aids, crop protection agents, active pharmaceutical ingredients, vitamins, fertilizers and/or other nutrients.

Active pharmaceutical ingredients which can be used are analgesics, antiallergics, antibiotics, antiemetics, antiseptics, antihistamines, antihypertensives, appetite suppressants, cardiac remedies, chemotherapeutic agents, enzyme products, hormones, immunomodulators, inoculations, local anesthetics, psychoactive drugs, spasmolytics, virustatics, vitamins and cytostatics.

Suitable active ingredients are in particular diamorphine, alfentanil, sufentanyl, pentazocine, buprenorphine, nefopam, flupirtine, tramadol, oxycodone, metamizole, propyphenanzone, phenazone, nifenazone, phenylbutazone, oxyphenbutazone, mofebutazone, diflunisal, meptazinol, methadone, pethidine, meloxicam, fenbufen, mefenamic acid, tenoxicam, azapropazone, piritramide, tramadol, amantadine, benzotropine, procyclidine, moclobemide, tranylcypromide, maprotiline, doxepin, opipramol, desipramine, imipramine, fluroxamine, paroxetine, trazodone, viloxazine, fluphenazine, perphenazine, promethazine, thioridazine, triflupromazine, prothipendyl, tiotixene, chlorprothixene, pipamperone, pimozide, fenethylline, trifluoperazine, thioridazine, oxazepam, alprazolam, clobazam, piracetam, melfalan, cyclophosphamide, trofosfamide, chlorambucil, lomustine, busilfan, prednimustine, mercaptopurine, thioguanine, hydroxycarbamide, altretamine, procarbazine, lisuride, methysergide, pizotifen, roxatidine, pirenzipine, proglumide, bromopride, pheniramine, dimethindene, tritoqualine, loratadine, doxylamine, mequitazine, dexchlorpheniramine, triprolidine, oxatomide, moxonidine, doxazosine, urapidil, dihydralazine, deserpidine, alprenolol, bupranolol, penbutolol, esmolol, ciliprolol, metipranolol, nadolol, quinapril, fosinopril, cilazapril, democlocycline, lymecycline, oxytetracycline, sulfamethopyrazine, aerosoxacin, becampicillin, piperacillin, pivampicillin, cloxacillin, flucloxacillin, metronidazole, clindamycin, cefaclor, cefpodoxime, cephalexin, cefradine, pirbuterol, orciprenaline, clenbuterol, procaterol, choline theophyllinate, theophyllineethylenediamine, Ketofen, viquidil, procainamide, mexiletine, tocainide, ipratropium, tobutamide, gliquidone, gliboruride, tolazamide, acarbose and pharmaceutically active salts or esters of the aforementioned active ingredients, and combinations of two or more of these active ingredients or salts or esters thereof.

Examples of suitable active ingredients are acebutolol, acetylcysteine, acetylsalicylic acid, aciclovir, albrazolam, alfacalcidol, allantoin, allopurinol, ambroxiol, amikacin, amiloride, aminoacetic acid, amiodarone, amitriptyline, amlodipine, amoxicillin, ampicillin, ascorbic acid, aspartame, astemizole, atenolol, beclometasone, benserazide, benzalkonium hydrochloride, benzocaine, benzoic acid, betametasone, bezafibrate, biotin, biperidene, bisoprolol, bromacepam, bromhexine, bromocriptine, budesonide, bufexamac, buflomedil, buspirone, caffeine, camphor, captopril, carbamacipine, carbidopa, carboplatin, cefachlor, cefalexin, cefadroxil, cefazolin, cefixime, cefotaxime, ceftazidine, ceftriaxone, cefuroxime, celedilin, chloramhenicol, chlorhexidine, chlorpheniramine, chlortalidone, choline, ciclosporin, cilastatin, cimetidine, ciprofloxacin, cisapride, cisplatin, clarithromycin, clavulanic acid, clomibramine, clonazepam, clonidine, clotrimazole, codeine, cholestyramine, cromoglicic acid, cyanocobalamin, cyproterone, desogetrel, dexamethasone, dexpanthenol, dexthromethorphan, dextropropoxiphen, diazepam, diclofenac, digoxin, dihydrocodeine, dihyderoergotamine, dihydroergotoxin, diltiazem, diphenhydramine, dipyridamole, dipyrone, disopyramide, domperidone, dopamine, doxycycline, enalapril, ephedrine, epinephrine, ergocalciferol, ergotamine, erythromycin, estradiol, ethinylestradinol, etoposide, famotidine, felodipine, fenofibrate, fenoterol, fentanyl, flavin mononucleotide, fluconazole, flunarizine, fluorouracil, fluoxetine, flurbiprofen, furosemide, gallopamil, gem-fibrozil, gentaminicin, Gingko Biloba, glibenclamide, glipizide, glozapine, Glycyrrhiza Glabra, griseofulvin, guaifenesin, haloperidol, heparin, hyaluronic acid, hydrochlorothiazide, hydrocodone, hydrocortisone, hydromorphone, ibratropium hydroxide, ibuprofen, imipenem, indomethacin, iohexol, iopamidol, isosorbide dinitrate, isosorbide mononitrate, isotretionin, ketotifen, ketoconazole, ketoprofen, ketorolac, labatalon, lactulose, lecithin, levocarnitine, levodopa, levoglutamide, levonorgestrel, levothyroxine, lidocaine, lipase, lipramine, lisinopril, loperamide, lorazepam, lovastatin, medroxyprogesterone, menthol, methotrexate, methyldopa, methylprednisolone, metoclopramide, metoprolol, miconazole, midazolam, minocycline, minoxidil, misoprostol, morphine, multivitamins and minerals, N-methylephedrine, naftidrofuryl, naproxen, neomycin, nicardipine, nicergoline, nicotinamide, nicotine, nicotinic acid, nifedipine, nimodipine, nitrazepam, nitrendipine, nizatidine, norethisterone, norfloxacin, norgestrel, nortriptyline, nystatin, ofloxacine, omeprazole, ondansetron, pancreatin, panthenol, pantothenic acid, paracetamol, penicillin G, penicillin V, phenobarbital, phenoxifylline, phenoxymethyl-penicillin, phenylephrine, phenylpropanolamine, phenyloin, piroxicam, polymyxin B, povidone-iodine, pravastatin, prazepam, prazosin, prednisolone, prednisone, propafenone, propranolol, proxyphylline, pseudoephedrine, pyridoxine, quinidine, ramipril, ranitidine, reserpine, retinol, riboflavin, rifampicin, rutoside, saccharin, salbutamol, salcatonin, salicylic acid, simvastatin, somatropin, sotalol, spironolactone, sucralfate, sulbactam, sulfamethoxazole, sulfasalazine, sulpiride, tamoxifen, tegafur, teprenone, terazosin, terbutaline, terfenadine, tetracycline, theophylline, thiamine, ticlopidine, timolol, tranexamic acid, tretinoin, triamcinolone acetonide, triamteren, trimethoprim, troxerutin, uracil, valproic acid, vancomycin, verapamil, vitamins E, zidovudine.

Further suitable active ingredients are prochlorperazine edisylal, iron-II sulfate, aminocaproic acid, potassium chloride, mecamylamine hydrochloride, procainamide hydrochloride, amphetamine sulfate, benzphetamine hydrochloride, isoporterenol sulfate, methamphetamine hydrochloride, phenmetrazine hydrochloride, bethanechol chloride, methacholine chloride, pilocarpine hydrochloride, atropine sulfate, methascopolamine bromide, isopropamide iodide, tridihexethyl chloride, phenformin hydrochloride, methylphenidate hydrochloride, oxprenolol hydrochloride, metroprolol tartrate, cimetidine hydrochloride, diphenidol, meclizine hydrochloride, prochlorperazine maleate, phenoxybenzamine, thiethylperazine maleate, anisindone, diphenadione, erythritol tetranitrate, dizoxin, isofurophate, acetazolamide, methazolamide, bendroflumethiazide, chlorpropamide, tolazamide, chlormadinone acetate, phenaglycodol, aluminum-aspirin, methotrexate, acetyl-sulfioxazole, progestins, estrogenic steroids, progestatinal steroids, corticosteroids, 17-β-estradiol, ethinylestradiol 3-methyl ester, hydro-corticosterone acetate, methyltesterone, 17-α-hydroxyprogesterone acetate, 19-norprogesterone, norethindrone, progesterone, norgesterone, norethynodrel and others.

Further examples of active ingredients are fenoprofen, sulindac, indoprofen, nitroglycerine, timolol, alprenolol, imipramine, chlorpromazine, dihydroxy-phenylalanine, pivaloxyloxyethyl ester of α-methyldopa hydrochloride, calcium gluconate, iron-II lactate, vincamine, phenoxybenzamine, blockers and the like. The active ingredients are disclosed in "Pharmaceutical Sciences" by Remington, 14th edition, 1979, Mack Publishing Co., Easton, Pa.; "The Drug, The Nurse, The Patient, Including Current Drug Handbook", 1974-1976, by Falconer et al, Saunder Co., Philadelphia, Pa., and "Medical Chemistry", 3rd edition, volume 1 and 2, by Burger, Wiley-Interscience, New York.

Representative medicaments which can be administered to warm-blooded animals, for example ruminants, with the aid of the inventive dosage form are inter alia anthelmintics such as mebendazole, levamisole, albendazole, cambendazole, fenbendazole, parbendazole, oxfendazole, oxybendazole, thiabendazole, trichlorfon, praziquantel, morantel and pirantel, and the like; antiparasitic agents such as avermectins and ivermectin as indicated in U.S. Pat. Nos. 4,199,569 and 4,389,397 (Merck) and in "Science", volume 221, pp. 823-828, 1983, where these ivermectin antiparasitic agents are indicated as suitable for helping to control worms normally occurring in mammals, such as roundworms (eel worms), long worms and the like, and also that ivermectin is suitable for the treatment of insect infections such as maggots, lice, mite mange and the like; antimicrobial agents such as chlorotetracycline, oxytetracycline, tetracycline, gentamicin, streptomycin, dihydro-streptomycin, bacitracins, erthromycin, ampicillins, penicillins, cephalosporins and the like; sulfur-containing medicaments (sufa drugs) such as sulfamethazine, sulfathiazole and the like; growth stimulants such as Monesin® sodium and Elfazepam®; antiflea agents (defleaing agents) such as dexamethazone and flumethazone; agents influencing digestion in the rumen and ionophores, such as lasalocid, virginamiycin, salinomycin and ronnel; minerals such as copper oxide, cobalt sulfate, potassium iodate, zinc oxide, manganese sulfate, zinc sulfate, selenium, sodium selenite, beneficial mineral salts and the like; antibloating agents such as organic polysiloxanes; hormonal growth additions such as stilbestrol; vitamins such as vitamins A and D; with 500 000:100 100 IU/f, vitamin E with 500 000 IU/f and the like; antienteritis agents such as furazolidone, growth factors, nutrient additions such as lysine monohydrochloride, methionine, magnesium carbonate and the like; β agonists, elenbuterol and the like, and chemical markers such as chromium oxide, and salts of ytterbium and erbium.

The locally acting active ingredients further include fungicides such as amphotericin B, antibiotics such as penicillins, cephalosporins, erythromycin, tetracycline, aminoglycosides, antiviral compounds such as acyclovir, idoxuridine, breath improvers such as chlorophyll, tissue growth-inhibiting compounds, anticaries compounds such as metal fluorides, especially sodium monofluorophosphate, tin fluoride, amine fluoride, analgesics such as methyl salicylate, local anesthetics such as benzocaine, oral antiseptics such as chlorhexidine and its salts, hexylresorcinol, dequalinium chloride, cetylpyridine chloride, antiinflammatory agents, hormones such as estriol, antiplaque compounds such as chlorhexidine and its salts, octenidine, or mixtures of thymol, menthol, methyl salicylate, eucalyptol, buffer compounds such as potassium phosphate, calcium carbonate, sodium bicarbonate, sodium hydroxide and potassium hydroxide, and desensitizers for teeth such as, for example, potassium nitrate.

Further suitable active ingredients are disinfectants such as chlorine compounds, especially calcium hypochlorite, an insecticide, pesticide, herbicide, fungicide, or growth promoters or fertilizers such as, for example, nitrogen-containing compounds, especially urea, urea-formaldehyde compounds, calium nitrate, calium sulfate, calium chloride, ammonium nitrate, ammonium suflate, monoammonium phosphate, dibasic ammonium phosphate, ammonium-phosphoric acid compounds, trace elements for food products such as iron, zinc, manganese, copper, boron, molybdenum or mixtures thereof.

Active ingredients suitable for the inventive dosage form are also steroid hormones such as:
progestationally active steroid hormones such as, for example, 13-ethyl-17β-hydroxy-18,19-dinor-17α-pregn-4-en-20yl-3-one, 13-ethyl-17β-hydroxy-18,19-dinor-17α-pregna-4,15-dien-20yn-3-one (=gestodene), 13-ethyl-17β-hydroxy-11-methylene-18,19-dinor-17α-pregn-4-en-20yne or 13-ethyl-11-methylene-17β-hydroxy-18,19-dinor-17α-pregn-4-en-3-one (3-keto-desogestrel), estrogenically active steroid hormones 3-hydroxy-1,3,5-(10)-estratrien-17-one estrone), 1,3,5-(10)-estratriene-3,17β-diol or 1,9-nor-17α-pregna-1,3,5-(10)-trien-20yne-3,17β-diol, 17β-hydroxy-19-nor-17α-pregn-4-en-20yn-3-one, 14α,17α-ethano-1,3,5-(10)-estratriene-3,17β-diol (=cyclodiol) and 14α,17α-ethano-1,3,5-(10)-estratriene-3,16α,17β-triol (=cyclotriol) and combinations of these progestins and estrogens.

Androgenically active steroid hormones such as 17β-hydroxy-4-androsten-3-one (=testosterone) and its esters or 17β-hydroxy-1α-methyl-5α-androsten-3-one (=mesterolone).

Antiandrogenically active steroid hormones such as 17α-acetoxy-6-chloro-1β,2β-dihydro-3H-cyclopropa[1,2]-pregna-1,4,6-triene-3,20-dione.

Corticoids such as 11β,17α,21-trihydroxy-4-pregnene-3,20-dione, 11β,17α,21-trihydroxy-1,4-pegnadiene-3,20-dione, 11β,17α,21-trihydroxy-6α-methyl-1,4-pregna-triene-3,20-dione and 6α-fluoro-11β,21-dihydroxy-16α-methyl-1,4-pregnadiene-3,20-dione (=diflucortolone) and esters thereof.

Further suitable active ingredients are:
ergoline derivatives such as lisuride, [3-(9,10-didehydro-6-methyl-8α-ergolinyl)-1,1-diethylurea], bromolisuride [=3-(2-bromo-9,10-dehydro-6-methyl-8α-ergolinyl-1,1-diethylurea], terguride [=3-(6-methyl-8α-ergolinyl-1,1-diethylurea] and proterguride [=3-(6-propyl-8α-ergolinyl)-1,1-diethylurea].

Antihypertensives such as 7α-acetylthio-17α-hydroxy-3-oxo-4-pregnene-21-carboxylic acid γ-lactone and 7α-acetylthio-15β,16β-methylene-3-oxo-17α-pregna-1,4-diene-21,17-carbolactone (=mespirenone).

Anticoagulants such as 5-[hexahydro-5-hydroxy-4-(3-hydroxy-4-methyl-1-octen-6-ynyl)-2(1H)-pentalenyl-idene)] pentanoic acid (=iloprost) or (Z)-7-[(1R,2R,3R,5R)-5-chloro-2-hydroxy-2-[(E)-(3R)-3-hydroxy-4,4-dimethyl-1-octenyl]cyclopentyl]-5-heptenoic acid (=nocloprost).

Psychoactive drugs such as 4-(3-cyclopentyloxy-4-methoxyphenyl-2-pyrrolidone rolipram) and 7-chloro-1,3-dihydro-1-methyl-5-phenyl-2H-1,4-benzo-diazepin-2-one.

The dosage form of the invention consisting of layers based on crosslinked hydrophilic polymers, in particular with large amounts of glycerol (>40% by weight) is at risk of microbial decomposition if it is stored under nonsterile conditions for a prolonged period. In this case, preservatives are necessary. Suitable preservatives are all conventional preservatives. Possible preservatives belong inter alia to the group of alcohols (e.g. chlorobutanol, phenylethyl alcohol or benzyl alcohol), acids (e.g. sorbic acid, benzoic acid or boric acid), PHB esters (e.g. parabens), phenol derivatives (e.g. phenol, cresol or chlorocresol), quaternary compounds or quaternary ammonium compounds (quats) (e.g. benzalkonium chloride), organo-Hg compounds (e.g. thiomersal, phenylmercury nitrate or phenylmercury borate) and guanides (e.g. chlorhexidine or chlorhexidine acetate). It is also possible to employ mixtures of at least two preservatives.

The inventive dosage forms in film form may have one or more layers. If the dosage forms in film form have multiple layers, they may have more than one active ingredient-containing and/or nutrient-containing layer, an adhesive layer and/or a covering layer.

The active ingredient-containing and/or nutrient-containing layer(s) in the inventive dosage form in film form is/are based on crosslinked hydrophilic polymers and comprise(s) glycerol. The active ingredient-containing and/or nutrient-containing layer(s) may comprise the active ingredient in a molecular and/or particulate form.

The release of active ingredient and/or nutrient from the active ingredient-containing and/or nutrient-containing layer or the further active ingredient-containing and/or nutrient-containing layers which are present can be controlled not only by the different active ingredient concentration and/or nutrient concentration but also by the degree of crosslinking of the hydrophilic polymers. Within an active ingredient-containing and/or nutrient-containing layer it is possible for example to control the release by a concentration gradient of the active ingredient and/or of the nutrient. A further possibility for influencing the release of active ingredient and/or nutrient is to provide a plurality of active ingredient-containing and/or nutrient-containing layers with different active ingredient and/or nutrient concentrations in the inventive dosage forms in film form. It is also possible moreover for active ingredient-free or nutrient-free layers, where appropriate composed of crosslinked hydrophilic polymers, to be present between the active ingredient-containing or nutrient-containing layers. It is thus possible for the active ingredient to be released rapidly and in an amount sufficient to achieve an immediate effect from a first active ingredient-containing layer based on hydrophilic polymers, while a longer-lasting release of active ingredient is made possible from further active ingredient-containing layers to achieve a prolonged effect.

The active ingredient-containing and/or nutrient-containing layer preferably has a thickness of 30-500 μm.

In order to ensure adequate adhesion of the dosage form of the invention on transmucosal or transdermal administration, it is possible either to incorporate a bioadhesive polymer in the active ingredient-containing and/or nutrient-containing layer, or to provide an additional layer as adhesive layer in the dosage form of the invention. An adhesive layer may consist of one or more of the known bioadhesive polymers such as, for example, polyacrylic acid derivatives. For example, the adhesive layer may consist of a mixture of optionally crosslinked hydrophilic polymers and a polyacrylic acid derivative or only of polyacrylic acid derivatives. Suitable bioadhesive polyacrylic acid derivatives are polyacrylic acids which are optionally partly in the form of the calcium salt and optionally crosslinked. Polyacrylic acids partly in the form of the calcium salt and crosslinked with divinylglycol are particularly preferred. Such products are available on the market as Polycarbophils®.

The adhesive layer may consist of a mixture of one or more of said bioadhesive polymers, such as, for example, ethylcellulose, especially if additional control of active ingredient release with the aid of the adhesive layer is desired.

The adhesive layer preferably has a thickness of from 10 to 100 μm.

The inventive dosage form in film form preferably also has a covering layer. The covering layer preferably consists of a water-insoluble polymer and is impermeable for the active ingredient and/or nutrient. This ensures unidirectional release of active ingredient and/or nutrient. With this unidirectional release, the active ingredient and/or nutrient is released only at the site of application.

The covering layer may be composed of crosslinked hydrophilic polymers, for example of hydroxypropylmethylcellulose crosslinked with tannin.

A further possibility is for the covering layer to be composed of at least one water-insoluble cellulose ether, preferably of alkylcellulose, particularly preferably of ethylcellulose, or of a cellulose ester, preferably cellulose acetate, and/or of a water-insoluble poly(meth)acrylate, preferably a poly (C1-4)alkyl(meth)acrylate, poly(C1-4)dialkylamino-(C1-4) alkyl(meth)acrylate and/or copolymers thereof, very particularly preferably a copolymer of ethyl acrylate/methyl methacrylate and/or a copolymer of ethyl acrylate/methyl methacrylate/trimethylammoniumethyl methacrylate chloride. The cellulose ethers, cellulose esters and/or poly(meth) acrylates may, where appropriate, comprise plasticizers.

In a preferred embodiment of the claimed invention, the covering layer is composed of ethylcellulose or of a copolymer of ethyl acrylate/methyl methacrylate/-trimethylammoniumethyl methacrylate chloride with a molar ratio of the respective monomers of 1:2:0.1, in both cases with a percentage amount of plasticizer, preferably triethyl citrates, of from 20 to 40% by weight based on the amount of polymer. A very particularly preferred covering layer consists of a copolymer of ethyl acrylate/methyl methacrylate with a molar ratio of the respective monomers of 2:1 (plasticizer addition not absolutely necessary in this case).

The covering layer preferably has a thickness of from 10 to 100 μm.

The inventive dosage form in film form can be covered with a protective layer before application.

The inventive dosage form in film form is produced by forming the active ingredient-containing and/or nutrient-containing layer or the active ingredient-containing and/or nutrient-containing layers, preferably from an aqueous solution of the hydrophilic polymers which comprises glycerol and of the active ingredient by application with simultaneous or subsequent exposure to the crosslinker, preferably as aqueous solution, and removal of the water by drying.

The covering layer can be produced by applying to the dried active ingredient-containing and/or nutrient-containing layer an aqueous dispersion such as a latex or pseudolatex dispersion of a water-insoluble polymer or a solution of such a polymer in a suitable organic solvent with subsequent removal of the water or organic solvent by drying and/or vacuum treatment.

If an adhesive layer is present on the inventive dosage form in film form, this is preferably composed of an aqueous solution or dispersion of polyacrylic acids which are optionally partly in the form of the calcium salt and optionally crosslinked.

The inventive dosage form in film form is preferably produced by building up the individual layers successively on a smooth surface, applying the film-forming polymer in each case together with the crosslinker which is optionally present, with the glycerol which is optionally present and with the active ingredient which is optionally present on each layer by spraying and drying as sublayers. The drying in this case preferably takes place simultaneously with the spraying. The sublayers preferably have a thickness of from 0.1 to 10 μm.

The spraying of the aqueous solution of hydrophilic polymers and of the aqueous solution of the crosslinker preferably takes place simultaneously, in which case the hydrophilic polymers and the crosslinker mix after the spraying and the polymer is then crosslinked in situ.

If the active ingredient and/or nutrient is present in one layer, the loading preferably takes place through the active ingredient and/or nutrient already being dissolved in the aqueous solution of hydrophilic polymers before this solution is brought together with the solution of the crosslinker.

The great variability of this procedure permits the layers to be built up in any sequence. It is thus possible to form first the adhesive layer, if present, or first the covering layer as basis for the subsequent layers.

The production process is preferably carried out employing an apparatus as described in DE 101 46 251. The corresponding disclosure is incorporated in the present disclosure.

This device comprises at least one spraying device, a dryer and at least one plate which is moved cyclically underneath the spraying device. The device preferably has a plurality of nozzles whose spray cones overlap.

Determination of the Plasticity by a Tensile Test

Tensile tests have been carried out to ascertain the mechanical properties, with the maximum elongation which can be achieved serving as measure of the plasticity of the dosage form of a material.

A TA.XT2i texture analyzer from Winopal (Germany) is employed to determine the maximum elongation and the tear strength. Pieces of the active ingredient-containing and/or nutrient-containing layer film with a length of 9.5 cm and a width of 1 cm are clamped at both ends with clamping jaws and slightly stretched so that the free tension length is 7 cm. The clamping jaws are provided with coatings on the surface which come into contact with the pieces in order to avoid premature tearing of the pieces at the clamps. If a piece tears, despite the coatings on the clamps, these values are not taken into account. The upper clamp pulls upwards at a constant speed of 0.5 mm/s. The force employed at every time during this, and the resulting elongation, is recorded by the texture analyzer. The force, the elongation and the time are then displayed and analyzed with the aid of software.

The tear strength of an investigated piece of film is the force acting on the piece of film just at the moment when the particular piece tears.

The maximum elongation is the extent of the elongation at the moment when the particular piece tears.

FIGURES

FIG. 1

Depiction of the force employed against the resulting elongation of a layer based on crosslinked hydroxypropylmethylcellulose without added plasticizer (comparative example 1) or 25% by weight, based on the total amount of crosslinked hydroxypropylmethylcellulose, of polyethylene glycol (comparative example 2) or sorbitol (comparative example 3) or glycerol (example 5). The films with glycerol show a larger maximum elongation and thus greater plasticity than the films with polyethylene glycol or sorbitol.

FIG. 2

Depiction of the force employed against the resulting elongation of a layer based on crosslinked hydroxypropylmethylcellulose with 20% by weight (example 6) or 50% by weight (example 7), based on the total amount of crosslinked hydroxypropylmethylcellulose, glycerol. With a larger amount of glycerol there is a greater maximum elongation which can be achieved and a greater plasticity of the layers. Films with 50% glycerol show a tear strength exceeding 60 N.

FIG. 3

Depiction of the force employed against the resulting elongation of a layer based on crosslinked hydroxypropylmethylcellulose with 20% by weight, based on the total amount of crosslinked hydroxypropylmethylcellulose, glycerol (example 6) or triethylcitrate (comparative example 4). The films with glycerol show a larger maximum elongation which can be achieved and moreover a greater plasticity than the films with triethylcitrate.

EXAMPLES

Example 1

To produce the dosage form in film form, a solution of 10 g of hydroxypropylmethylcellulose, 5 g of glycerol, 1 g of the active ingredient prednisolone, and 484 g of water, and a solution of 2.5 g of tannin in 497.5 g of water were prepared. Using the apparatus described in DE 101 46 251, these two solutions were sprayed each with one nozzle simultaneously onto a glass plate and dried at 80° C., and the spraying step was repeated after formation of the respective sublayer several times until the layer thickness had reached 80 μm. The dosage form produced in this way was easy to handle and easy to apply to the human skin and to human mucous membranes, for example to the buccal mucosa.

Example 2 a) To produce the active ingredient-containing layer, a solution of 10 g of hydroxypropylmethylcellulose, 7.5 g of glycerol, 1 g of the active ingredient prednisolone, and 481.5 g of water, and a solution of 2.5 g of tannin in 497.5 g of water were prepared. Using the apparatus described in DE 101 46 251, these two solutions were sprayed each with one nozzle simultaneously onto a glass plate and dried at 80° C., and the spraying step was repeated after formation of the respective sublayer several times until the layer thickness had reached 200 μm.

b) A dispersion of 6 g of polyacrylic acid crosslinked with divinylglycol (Polycarbophil®) in 494 g of water was prepared. This dispersion was also applied using the apparatus indicated above in a multistep spraying of sublayers on the active ingredient layer until the layer thickness of the adhesive layer had reached 50 μm.

The dosage form produced in this way was easy to handle and easy to apply to the human skin and to human mucous membranes, for example to the buccal mucosa.

Example 3 a) To produce the covering layer, a solution of 10 g of hydroxypropylmethylcellulose, 6.25 g of glycerol and 483.75 g of water, and a solution of 2.5 g of tannin in 497.5 g of water were prepared. Using the apparatus described in DE 101 46 251, these two solutions were sprayed each with one nozzle simultaneously onto a glass plate and dried at 80° C., and the spraying step was repeated after formation of the respective sublayer several times until the layer thickness of the covering layer had reached 50 μm.

b) In the same manner as described in a), a solution of 10 g of hydroxypropylmethylcellulose, 6.25 g of glycerol, 2 g of prednisolone, as example of active ingredient, and 481.75 g of water, and a solution of 2.5 g of tannin in 497.5 g of water were applied using the same apparatus by multistep spraying of sublayers on the covering layer until the layer thickness of the active ingredient-containing layer had reached 100 μm.

The dosage form produced in this way was easy to handle and easy to apply to the human skin and to human mucous membranes, for example to the buccal mucosa.

Example 4 a) To produce the covering layer, a 10% strength aqueous latex of an ethylacryl/methyl methacrylate copolymer with a 2:1 molar ratio of the monomers, obtained by diluting 333.33 g of a 30% strength aqueous latex with 666.67 g of water, was employed. This dispersion was using the apparatus described in DE 101 46 251 in a multistep spraying in which the sublayers were produced in each of the steps until the layer thickness of the covering layer had reached 50 μm.

b) To produce the active ingredient-containing layer, a solution of 10 g of hydroxypropylmethylcellulose, 7.5 g of glycerol, 2 g of prednisolone, as example of active ingredient, and 480.5 g of water, and a solution of 2.5 g of tannin in 497.5 g of water were applied using the same apparatus by a multistep spraying of sublayers on the covering layer until a layer thickness of the active ingredient-containing layer had reached 300 μm.

c) A dispersion of 6 g of polyacrylic acid crosslinked with divinylglycol (Polycarbophil®) in 494 g of water was prepared. This dispersion was also using the apparatus indicated above in a multistep spraying in which the sublayers were produced in each of the steps until the layer thickness of the adhesive layer had reached 50 μm.

The dosage form produced in this way was easy to handle and easy to apply to the human skin and to human mucous membranes, for example to the buccal mucosa.

Example 5

To produce the dosage form in film form, a solution of 10 g of hydroxypropylmethylcellulose, 3.125 g of glycerol, 0.5 g of the active ingredient prednisolone, and 486.375 g of water, and a solution of 2.5 g of tannin in 497.5 g of water were prepared. Using the apparatus described in DE 101 46 251, these two solutions were sprayed each with one nozzle simultaneously onto a glass plate and dried at 80° C., and the spraying step was repeated after formation of the respective sublayer several times until the layer thickness had reached 300 μm.

The dosage form produced in this way was easy to handle and easy to apply to the human skin and to human mucous membranes, for example to the buccal mucosa.

Example 6

To produce the dosage form in film form, a solution of 10 g of hydroxypropylmethylcellulose, 2.5 g of glycerol, 0.5 g of the active ingredient prednisolone, and 487 g of water, and a solution of 2.5 g of tannin in 497.5 g of water were prepared. Using the apparatus described in DE 101 46 251, these two solutions were sprayed each with one nozzle simultaneously onto a glass plate and dried at 80° C., and the spraying step was repeated after formation of the respective sublayer several times until the layer thickness had reached 300 μm.

The dosage form produced in this way was easy to handle and easy to apply to the human skin and to human mucous membranes, for example to the buccal mucosa.

Example 7

To produce the dosage form in film form, a solution of 10 g of hydroxypropylmethylcellulose, 6.25 g of glycerol, 0.5 g of the active ingredient prednisolone, and 483.25 g of water, and a solution of 2.5 g of tannin in 497.5 g of water were prepared. Using the apparatus described in DE 101 46 251, these two solutions were sprayed each with one nozzle simultaneously onto a glass plate and dried at 80° C., and the spraying step was repeated after formation of the respective sublayer several times until the layer thickness had reached 300 μm.

The dosage form produced in this way was easy to handle and easy to apply to the human skin and to human mucous membranes, for example to the buccal mucosa.

Comparative Example 1

To produce the dosage form in film form without plasticizer, a solution of 10 g of hydroxypropylmethylcellulose, 0.5 g of the active ingredient prednisolone, and 489.5 g of water, and a solution of 2.5 g of tannin in 497.5 g of water were prepared. Using the apparatus described in DE 101 46 251, these two solutions were sprayed each with one nozzle simultaneously onto a glass plate and dried at 80° C., and the spraying step was repeated after formation of the respective sublayer several times until the layer thickness had reached 300 μm.

The dosage form produced in this way was difficult to apply to the human skin and to the human mucous membranes, for example to the buccal mucosa.

Comparative Example 2

To produce the dosage form in film form, a solution of 10 g of hydroxypropylmethylcellulose, 3.125 g of polyethylene glycol, 0.5 g of the active ingredient prednisolone, and 486.375 g of water, and a solution of 2.5 g of tannin in 497.5 g of water were prepared. Using the apparatus described in DE 101 46 251, these two solutions were sprayed each with one nozzle simultaneously onto a glass plate and dried at 80° C., and the spraying step was repeated after formation of the respective sublayer several times until the layer thickness had reached 300 μm.

The dosage form produced in this way was easier to apply to the human skin and to human mucous membranes, for example to the buccal mucosa, than the dosage form from Comparative example 1 (no plasticizer), but was more difficult to apply than the dosage form of Example 5 with 25% by weight, based on the total amount of crosslinked hydroxypropylmethylcellulose, of glycerol.

Comparative Example 3

To produce the dosage form in film form, a solution of 10 g of hydroxypropylmethylcellulose, 3.125 g of sorbitol, 0.5 g of the active ingredient prednisolone, and 486.375 g of water, and a solution of 2.5 g of tannin in 497.5 g of water were prepared. Using the apparatus described in DE 101 46 251, these two solutions were sprayed each with one nozzle simultaneously onto a glass plate and dried at 80° C., and the spraying step was repeated after formation of the respective sublayer several times until the layer thickness had reached 300 μm.

The dosage form produced in this way was easier to apply to the human skin and to human mucous membranes, for example to the buccal mucosa, than the dosage form from Comparative example 1 (no plasticizer), but was more difficult to apply than the dosage form of Example 5 with 25% by weight, based on the total amount of crosslinked hydroxypropylmethylcellulose, of glycerol.

Comparative Example 4

To produce the dosage form in film form, a solution of 10 g of hydroxypropylmethylcellulose, 2.5 g of triethyl citrate, 0.5 g of the active ingredient prednisolone, and 487 g of water, and a solution of 2.5 g of tannin in 497.5 g of water were prepared. Using the apparatus described in DE 101 46 251, these two solutions were sprayed each with one nozzle simultaneously onto a glass plate and dried at 80° C., and the spraying step was repeated after formation of the respective sublayer several times until the layer thickness had reached 300 μm.

The dosage form produced in this way was easier to apply to the human skin and to human mucous membranes, for example to the buccal mucosa, than the dosage form from Comparative example 1 (no plasticizer), but was more difficult to apply than the dosage form of Example 3 with 20% by weight, based on the total amount of crosslinked hydroxypropylmethylcellulose, of glycerol.

The invention claimed is:

1. A dosage form in film form for transmucosal or transdermal administration of at least one active ingredient and/or nutrient to a living creature comprising
at least one active ingredient-containing and/or nutrient-containing layer based on in-situ crosslinked hydrophilic polymers which comprises from 30% to 60% by weight of glycerol as plasticizer, based on the total amount of crosslinked hydrophilic polymers
characterized in that hydroxypropylmethylcellulose is used as hydrophilic polymer and the hydrophilic polymer has been crosslinked with tannin and/or a crosslinked, optionally partially neutralized polyacrylic acid.

2. The dosage form as claimed in claim 1, characterized in that the active ingredient-containing and/or nutrient-containing layer comprises at least one active pharmaceutical ingredient or one nutrient.

3. The dosage form as claimed in claim 2, characterized in that the active pharmaceutical ingredient is an active ingredient from the group of analgesics, antiallergics, antibiotics, antiemetics, antiseptics, antihistamines, antihypertensives, appetite suppressants, cardiac remedies, chemotherapeutic agents, enzymes, hormones, immunomodulators, inoculations, local anesthetics, psychoactive drugs, spasmolytics, virustatics, vitamins and cytostatics.

4. The dosage form as claimed in claim 2, characterized in that the nutrient is a fertilizer.

5. The dosage form as claimed in claim 1, characterized in that it has one or more layers.

6. The dosage form as claimed in claim 5, characterized in that it has at least one active ingredient-containing and/or nutrient-containing layer, one adhesive layer and/or one covering layer.

7. The dosage form as claimed in claim 6, characterized in that at least one active ingredient-containing and/or nutrient-containing layer has a concentration gradient of the active ingredient and/or of the nutrient.

8. The dosage form as claimed in claim 6, characterized in that the covering layer is impermeable for the active ingredient.

9. The dosage form as claimed in claim 1, characterized in that it is covered by a protective layer before application.

10. The dosage form as claimed in claim 1, characterized in that the living creature is a human or an animal.

11. The dosage form as claimed in claim 1, characterized in that the transmucosal or transdermal administration is buccal administration.

12. The dosage form as claimed in claim 1, characterized in that it has at least one active ingredient-containing and/or nutrient-containing layer, one adhesive layer and/or one covering layer.

13. The dosage form as claimed in claim 12, characterized in that at least one active ingredient-containing and/or nutrient-containing layer has a concentration gradient of the active ingredient and/or of the nutrient.

14. The dosage form as claimed in claim 13, characterized in that the covering layer is impermeable for the active ingredient.

15. The dosage form as claim in claim 14, characterized in that the ratio of hydrophilic polymer to crosslinker is from 2:1 to 5:1 by weight.

16. The dosage form as claimed in claim 15, characterized in that the at least one active ingredient and/or nutrient is prednisolone.

* * * * *